June 7, 1949. J. D. BROWNELL Plant Pat. 846
ROSE PLANT
Filed April 22, 1946
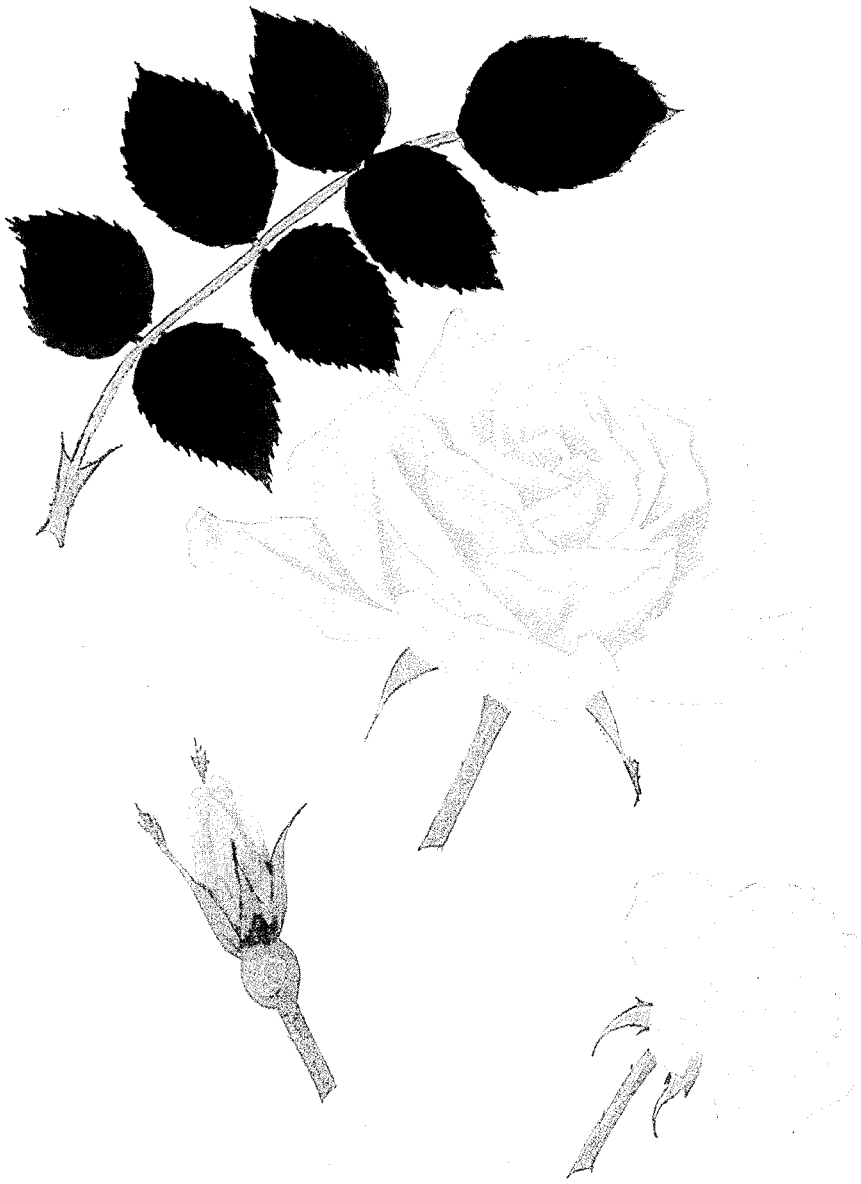
Josephine D. Brownell.
INVENTOR
BY
ATTORNEY Patented June 7, 1949

Plant Pat. 846

UNITED STATES PATENT OFFICE

846

ROSE PLANT

Josephine D. Brownell, Little Compton, R. I.

Application April 22, 1946, Serial No. 663,871

1 Claim. (Cl. 47—61)

My invention relates to rose plants, and especially to a new, original and distinct variety of the class known commercially as "hybrid teas" and is a variant in that class, being a *Rosa wichuraiana* hybrid tea, produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana*, of hardiness, or immunity from serious injury on account of cold temperatures prevailing in certain parts of the northern United States.

The red shades (ordinary dictionary definition) of its petals, in combination with the unique brilliance thereof and their tendency to hold these colors under exposure;

The novelty and variation within certain definite limits of the form of the bloom, its character of holding that form for a long time, and the petallage of the flowers.

Its character of fragrance;

Its unusual abundance of flowers, notably after early bloom time and until frost;

The intensity of its remontant and everblooming or reblooming character;

Its character of ascending in height by recurrent branching and progressively longer stems from the base;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of freedom from premature defoliation by black spot, under certain definite conditions of exposure, without any cultural control.

In the accompanying drawing forming a part of this specification I have shown my new rose in its natural colors, that is as near as is possible to do so artificially.

My new rose is otherwise described as follows:

*Essential information*

Type: Hybrid tea, *Rosa wichuraiana* hybrid, dwarf to ascending to tall to climber, for garden display, cut flower and forcing or growing under glass.

Class: Hybrid tea crossed with *Rosa wichuraiana*, further restricted by originator to include only those varieties that can survive moderately low sub-zero temperatures.

Breeding: This variety was produced and bred by me and under my direction by propagation and cross pollenation.

It came into being as a seedling grown from a seed borne on a plant of the variety "Pink Princess," Plant Patent Number 549, a hardy hybrid tea rose produced by me and under my direction, and the pollen parent of this new rose was the variety "Crimson Glory," Plant Patent Number 105.

The pollenation that fertilized the seed that grew into this new rose, as well as the pollenation that produced one of its parents was directed by me and was performed by emasculating flowers and placing thereon a bag protecting them from self and foreign pollen. These bags were later removed and the flowers were hand pollenated with a camel's hair brush and the bags immediately replaced. The date of this pollenation was July 7, 1944 [1]. The seed was planted under my direction on December 21, 1944, and the date of the first flower was July 8, 1945.

The plant and flower seemed to be of unusual merit and I have since made and directed extensive propagations and tests thereof.

Plants of this variety budded from this seedling onto *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1944–45 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one to two or three and frequently more on each stem, in the usual hybrid tea type of cluster. The pedicels and peduncles are medium in diameter and length, nearly erect, stiff, almost smooth, free from large prickles and bristles but with a few very small prickles varying to small hairs. Stems are long, diameter medium to notably stiff and rigid. The angle at which the stems seek to grow is about 20 degrees from the gravitational influence.

Quantity of bloom: Free to abundant, being cumulative in quantity from year to year as the plant increases in size, notably free flowering through the summer.

Fragrance: The fragrance of my new rose is an outstanding and distinctive characteristic, under certain environmental conditions it is comparable with the sweet fragrance of certain carnations, and under other conditions, the fragrance suggests that of sweet spices.

Bud: Neck normal as described, opens well, being little to not at all affected by hot or wet weather or both, as to color and form, except at very

[1] This and other dates herein are approximate.

high temperatures the color is less intense and the form of the petals is less recurled.

Before the calyx breaks the size is medium, form moderately pointed to ovoid, occasionally with one or more sepals having foliaceous parts extending beyond the apex of the calyx, pointed, serrate appendage on one and sometimes each side of some of the sepals, otherwise the sepals are usually normal and regular, tapering to lanceolate, at their apex, turning back nearly perpendicular to the pedicel as the bud opens.

Color of the bud as the calyx and petals open: both sides of outer petals vary between Rose Red [1] and Rose color, inner petals as they begin to open are both sides slightly nearer Spectrum Red.

Bloom: As the bud opens and the flower develops to maturity the color on both sides of petals slowly changes toward "Tyrian Pink."

The flower is normally 3½ to 5 inches in diameter when fully open, infrequently more or less; petals average between 35 and 40, frequently some smaller petals and petaloids in the center, variable in number.

The flower opens high centered, usually somewhat recurled outward in dry weather and more recurled in high humidity, showing stamens and pistils when fully open. The petals are variable from obovate to ovate to irregular and inner petals frequently with surfaces variously warped and crinkled and edges especially of the smaller petals somewhat irregular. Texture is medium both sides slightly satiny. The time of opening in favorable conditions is two to three days.

The petals are substantial and after about five days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity of wet weather.

Productive organs: *Stamens* variable in quantity, quantity, medium in length and slightly uneven.

*Anthers,* nearly Antimony yellow turning to Sofrano Pink.

*Filaments,* nearly Mustard Yellow.

*Pistils* are several of slightly uneven length, averaging around one-third inch long and numbering around fifty.

*Ovaries* are usually all inclosed.

*Hips* frequently develop to ovoid to globular, color comparable with under side of leaves with variable colored overlay on the side exposed to the sun, moderately smooth; walls, thin, fleshy.

*Sepals* are persistent and break off easily after maturity.

*Seeds* vary in number, around ten.

*Plant*

Foliage: Is abundant, of compound leaves of three to five leaflets near the flower, five leaflets lower down the stems and frequently seven leaflets nearer the base. Size of leaflets medium, averaging in size about ⅘ as large as the average hybrid tea leaflets. As the plants develop in size some of the leaflets develop to larger than the size described above. Form of leaflets usually ovate with apex moderately acute, base rounded frequently very slightly acute, edges with serrations moderately irregular to normal and medium in size.

[1] The color names herein unless otherwise designated are from "Color Standards," by Robert Ridgway.

The color of the upper surface at the time of bloom is Forest Green to Varley's Green, underside about Bice Green.

The stipules are medium from about one-half to three-quarters of an inch long, medium width about ¼ inch wide, with tips terminating in points. The inner edges of these tips form an angle of about 90°. The edges have many very short minute hairs.

Stems are medium as the plant develops, color Bice Green, side exposed to sun occasionally shaded with trace of Dahlia Carmine.

The prickles are nearly Dahlia Carmine to slightly variable, turning to lighter and more colorless.

Growth: Habit is hybrid tea type of growth ascending by branching and growth from the base.

Winter resistance: From tests at Little Compton, Rhode Island, this new rose plant compares in winter resistance with that of the Sub-Zero hybrid tea "Pink Princess."

Comparisons: I know of no *Rosa winchuraiana* hybrid tea that closely resembles this new rose. Red Robin has more depth of color, less petals and the bloom is usually smaller. Tomkins Red is much deeper in color, a smaller flower and has less petals. Of the non-wichuraiana hybrid teas the bloom of my new rose more nearly resembles that of Etoile de Holland, but is more resistant to winter injury and to defoliation on account of blackspot, and the fragrance is more distinctive, and of a sweeter and more unusual character.

My new rose variety in comparison with Application Number 663,870, filed April 22, 1946, normally grows its stems at an angle of about 28 degrees in relation to the gravitational influence and the variety of Application Number 663,870 normally grows its stems at an angle of about 5° to the same.

My new rose has about half as many petals, much more loosely and informally arranged and the blooms open more widely to show the stamens and are not so tightly compact, and the color is very much less intense. The stems average much smaller in diameter, being rigid and branch more. The influence of sunshine on the petals produces a fragrance of considerable intensity, closely resembling that characteristic of the carnation, and the fragrance of the other variety more closely resembles that of the China tea.

My new rose in comparison with application 663,868, filed April 22, 1946, normally grows its stems at about 28 degrees in relation to the gravitational influence as compared with an angle of about 45° of the other in relation to the same.

The red color of my new rose is very much less intense, the petals are very much less in number, more loosely and informally arranged and in the sunshine produce a fragrance much more resembling that characteristic of the carnation.

I claim:

The hardy hybrid *Rosa wichuraiana* hybrid tea rose plant variety characterized by its resistance to winter injury, with leaves frequently of seven leaflets, of light red shades, averaging about 35 petals informally arranged that open to show the stamens, of fragrance closely resembling that of the carnation, all substantially as described.

JOSEPHINE D. BROWNELL.

No references cited.